United States Patent
Aubin et al.

(10) Patent No.: US 8,409,258 B2
(45) Date of Patent: Apr. 2, 2013

(54) FUSIONLESS VERTEBRAL PHYSEAL DEVICE AND METHOD

(75) Inventors: Carl-Éric Aubin, Saint-Lambert (CA); John F. Sarwark, Glenview, IL (US); Eliane Schmid, Marin (CH); Stefan Parent, Saint-Lambert (CA)

(73) Assignees: Polyvalor, Limited Partnership (CA); Valorisation HSJ, Limited Partnership (CA)

( * ) Notice: Subject to any disclaimer, the term of this patent is extended or adjusted under 35 U.S.C. 154(b) by 1282 days.

(21) Appl. No.: 12/131,699

(22) Filed: Jun. 2, 2008

(65) Prior Publication Data
US 2009/0030518 A1   Jan. 29, 2009

Related U.S. Application Data

(60) Provisional application No. 60/941,511, filed on Jun. 1, 2007.

(51) Int. Cl.
*A61F 2/44* (2006.01)

(52) U.S. Cl. .................................. 606/280; 606/247

(58) Field of Classification Search ............... 606/247, 606/280
See application file for complete search history.

(56) References Cited

U.S. PATENT DOCUMENTS

| | | | | |
|---|---|---|---|---|
| 5,395,372 A * | 3/1995 | Holt et al. | ............... | 606/86 B |
| 5,423,816 A * | 6/1995 | Lin | ............... | 606/247 |
| 6,156,067 A * | 12/2000 | Bryan et al. | ............... | 623/17.15 |
| 6,214,005 B1 * | 4/2001 | Benzel et al. | ............... | 606/250 |
| 6,783,531 B2 * | 8/2004 | Allen | ............... | 606/75 |
| 6,966,911 B2 * | 11/2005 | Groiso | ............... | 606/75 |
| 6,974,479 B2 * | 12/2005 | Trieu | ............... | 623/17.11 |
| 7,341,591 B2 * | 3/2008 | Grinberg | ............... | 606/75 |
| 7,618,441 B2 * | 11/2009 | Groiso | ............... | 606/248 |
| 7,635,389 B2 * | 12/2009 | Yu et al. | ............... | 623/17.15 |
| 2005/0125066 A1 * | 6/2005 | McAfee | ............... | 623/17.16 |
| 2005/0261773 A1 * | 11/2005 | Ferree | ............... | 623/17.16 |

OTHER PUBLICATIONS

Betz RR et al. An Innovative Technique of Vertebral Body Stapling for the Treatment of Patients with Adolescent Idiopathic Scoliosis-:Spine 2003; 255-265.
Betz RR et al. Vertebral Body Stapling Procedure for the Treatment of Scoliosis in the Growing Child. Clinical Orthopaedics and Related Research 2, 2005; 434:55-60.
Wall EJ et al. Endoscopic Mechanical Spinal Hemiepiphysiodesis Modifies Spine Growth Spine, 2005; 30:10, 1148-1153.
Braun JT et al. Three-Dimensional Analysis of 2 Fusionless Scoliosis Treatments: A Flexible Ligament Tether versus a Rigid-Shape Memory Alloy Staple Spine2006; 31:3,262-268.
Braun JT et al. Creation of an Experimental Idiopathic-Type Scoliosis in an Immature Goat Model Using a Flexible Posterior Asymmetric Tether Spine 2006; 31: 13, 1410-1214.
Akyuz E et al Static Versus Dynamic Loading in the Mechanical Modulation of Vertebral Growth Spine, 2006; 31:25, E952-E958.

(Continued)

*Primary Examiner* — Ralph Lewis
(74) *Attorney, Agent, or Firm* — Quarles & Brady LLP (57) ABSTRACT

An intravertebral device for modulating vertebral growth without changing spinal mobility or compressing the intervertebral disc. By implanting the device around the vertebral growth plate, on the convex side of the curvature, a compression is induced on one side of the growth plate during the vertebral growth. This local growth modulation decreases significantly the vertebral wedging and corrects the global deformity of the spine. The device provides a minimally invasive and fusionless way of correcting spinal curvatures while preserving the intervertebral disc.

6 Claims, 11 Drawing Sheets

OTHER PUBLICATIONS

Grunhagen T et al. Nutrient Supply and Intervertebral Disc Metabolism J. Bone Joint Surg. Am. 2006; 88:30-35.

Stokes IAF et al. Modulation of vertebral and tibial growth by compression loading: diurnal versus full-time loading. Journal of Orthopaedic Research 2005; 23:188-195.

Stokes IAF et al. Mechnical Modulation of Vertebral Body Growth: Implications for Scoliosis Progression. Spine 1996; 21:1161-1167.

Hunziker EB, Schenk RK, Physiological Mechanisms adopted by chondrocye regulating longitudinal bone growth in rats Journal of Physiology 1989; 414: 55-71.

Alvares et al. Different bone growth rates . . . Proximal Growth Plates of the Rat Tibia Journal of Bone and Mineral Research 2000; 15:1, 82-94.

* cited by examiner

FIG_6A

⊢————⊣3mm

FIG_6B

⊢————⊣3mm

FIG_6C

FUSIONLESS VERTEBRAL PHYSEAL DEVICE AND METHOD

CROSS REFERENCE TO RELATED APPLICATIONS

This application claims priority on U.S. provisional application Ser. No. 60/941,511, filed on Jun. 1, 2007. All documents above are incorporated herein in their entirety by reference.

FIELD OF THE INVENTION

The present invention relates to vertebral physeal device and method. More specifically, the present invention is concerned with a fusionless vertebral physeal device and method inducing spinal growth modulation.

BACKGROUND OF THE INVENTION

In the past years there have been many attempts to develop and test fusionless devices for correcting spinal deformities[1-6]. They propose a minimally invasive approach which maintains a certain spinal flexibility. Depending on the design of these implants, they engender different local stiffening of the spine.

For example, Wall et al[3] introduced rigid 2 prongs vertebral staples fixed to two adjacent vertebral bodies slowing down growth on one side of the spine. They were tested on a pig model and showed the induction of significant spinal curvature (reverse problem).

Braun et al[4-6] tested two different fusionless scoliosis treatments in spinal curvatures induced by an asymmetric tether in a goat model: a flexible ligament tether attached to bone anchors and a rigid-shape memory alloy staple with 2 prongs. Both systems allowed successfully correcting the deformity by growth modulation. This shape memory alloy stapling technique, with a 2- and 4-prongs design, was also used by Betz et al. in a pilot study in humans for the treatment of AIS[1,2].

Previously explored solutions to hinder growth of the vertebral plate, which corresponds to epiphyseal cartilage at which new bone formation occurs to lengthen long bones during their growth phase, as an attempt to correct scoliosis include, for example, direct growth plate section using a scalpel, use of lasers to locally harm the vertebral growth plate, local inducement of a current through the vertebral growth plate to suppress growth.

Such techniques have shown their capacity to modulate the growth and correct spinal deformities. However, since they all span the intervertebral disc space, they induce changes of the spine kinematics and compression on the disc. Such effects were shown to alter the exchange of nutrients by diffusion and waste inside the disc[7], and may lead to disc degeneration.

Therefore, there is a need in the art for a vertebral physeal device and method.

The present description refers to a number of documents, the content of which is herein incorporated by reference in their entirety.

SUMMARY OF THE INVENTION

More specifically, in accordance with the present invention, there is provided a spinal growth modulation device, comprising a first part adapted to be inserted between a growth plate of a vertebral body and an adjacent intervertebral disk, and a second part adapted to be anchored into the vertebral body, the second part and the first part being connected by a length of material, the first part applying a force on the growth plate of the vertebral body as the growth plate of the vertebral body grows.

There is further provided a method for modulating growth of a target vertebral body of a spine, by inserting a first part between a growth plate of the target vertebral body and an associated intervertebral disc and securing the first part in contact with the growth plate of the target vertebral body by anchoring a second part to the vertebral body, the second part being connected to the first part by a length of material.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

A device according to an embodiment of a first aspect of the present invention will first be described.

Figure 1:
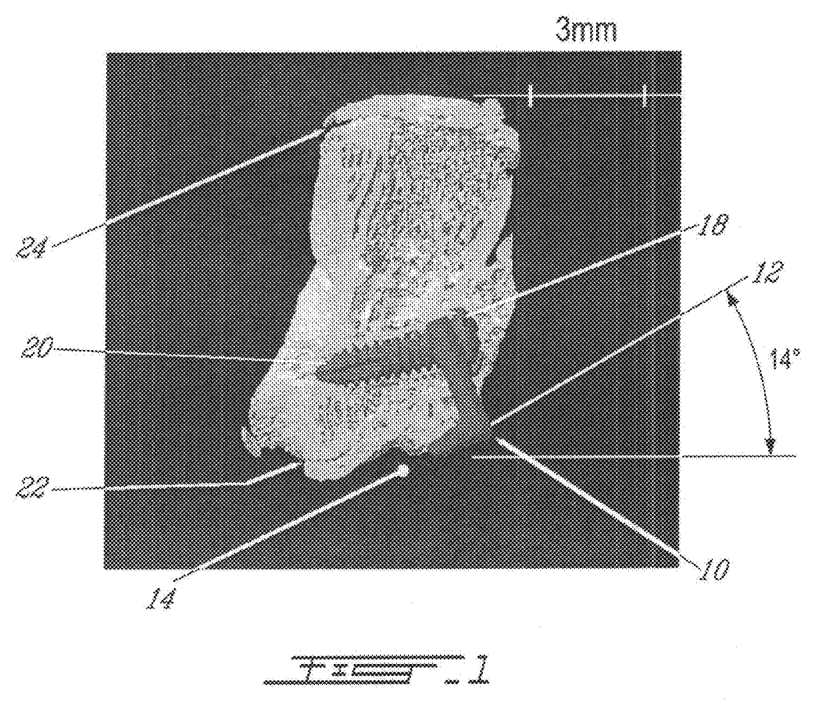
FIG. 1 shows a first embodiment of a device according to an embodiment of a first aspect of the present invention, in position on a caudal vertebra of a rat.

In FIG. 1, the device 10 is shown as comprising a first part 12 designed to fit between the growth plate of a vertebral body and its associated intervertebral disc 14 (in the tail of a rat), and a second part anchored in the vertebral body.

The device first part is shown as a prong 12, and the device second part is shown as a screw 20, inserted in a hole 18 in a length of material connecting the prong 12 and the screw 20. The screw 20, such as a 1 mm diameter maxillofacial-type screw for example, fixes the device 10 to the vertebral body.

The device 10 is made in a biocompatible material strong enough to resist the growth of vertebrae, such as titanium (grade 5, 6Al4V), surgical stainless steel for example.

Tests were performed on straight vertebral segments, to assess the deformation effect of the device.

Figure 4:
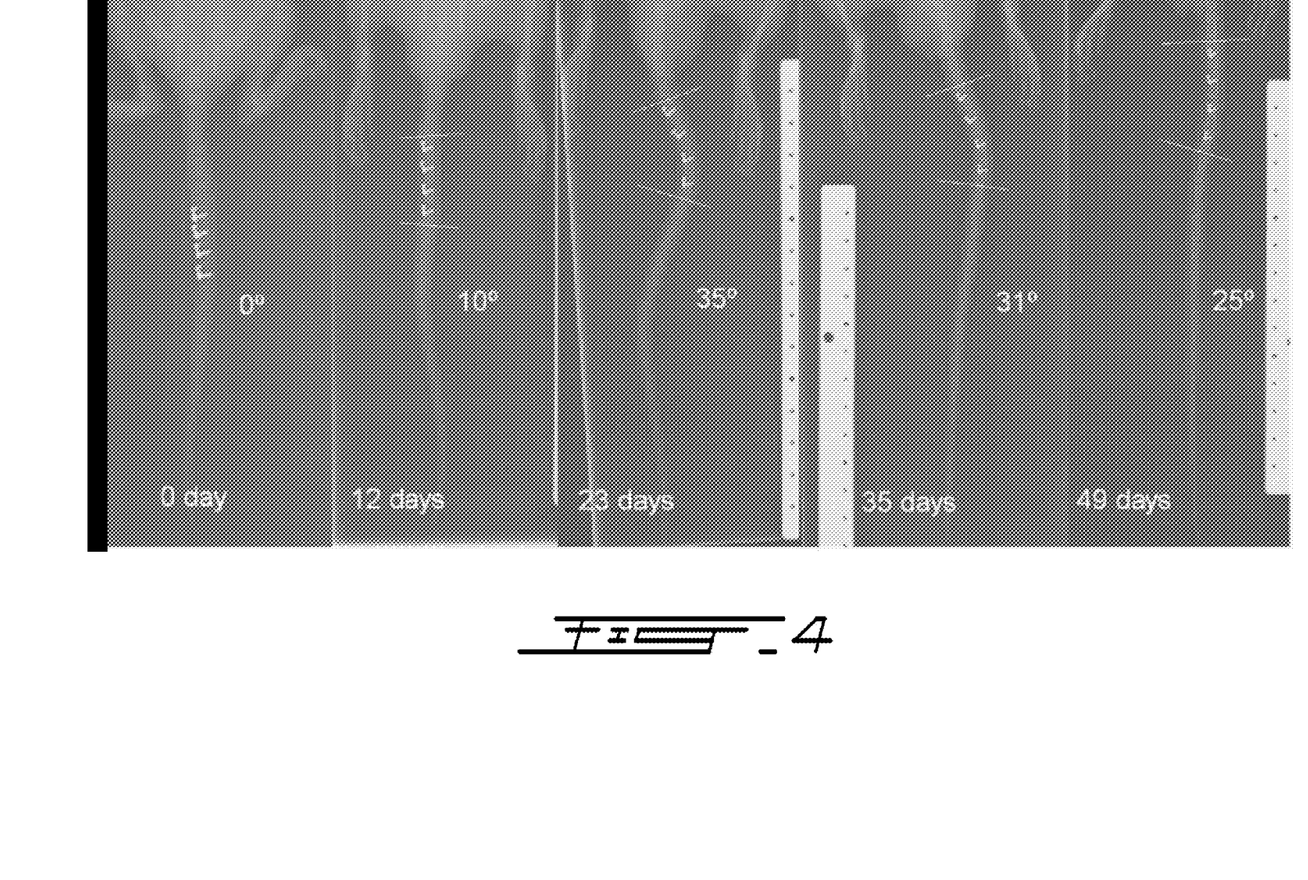
FIG. 4 shows global growth deformations in the tail of rat 5 presenting a complete growth modulation response, showing the evolution of the curvature in time.

As illustrated in FIG. 1, showing an effective growth modulation of the $7^{th}$ caudal vertebra in Rat 18 (3D reconstruction of micro CT Scan images, after sacrifice), the device 10 spans only one growth plate 22 of the vertebral body, i.e. the prong 12 is positioned between the growth plate 22 of the vertebral body and its associated intervertebral disc 14, while the screw 20 is positioned into the vertebral body comprised between the growth plate 22 of the vertebral body and the growth plate 24 of the vertebral body. As a result, the growth plate 22 the vertebral body is captured between the prong 12 and the vertebral body, on one side of the spine, the device 10 thus stopping or retarding the longitudinal growth of the endplate 22 on this side of the vertebra while permitting unrestrained growth of the endplate 22 on the opposite side of the spine. As can be see in FIG. 1, the device induces a wedged vertebra (Hueter-Volkmann principle). As shown later in FIG. 4, the device induces a spinal curvature, the instrumented side becoming concave.

The device was further tested on an animal model by inducing such a spinal deformity (inverse approach compared to treatment of spine deformation), to analyze the growth modification and to verify that the disc's physiology is viable.

The chosen animal model was the rat tail because of the accessibility to the caudal vertebrae and numerous studies of growth modulation done on this model[8,9]. Rats' caudal vertebrae, as many others animals' vertebrae, have a second ossification center[9] and the new concept of this device was adapted to fit the physiology and size of these vertebrae.

A study was conducted on 21 immature rats divided into 3 groups, including 1) an experimental group (n=11) in which the devices were installed on four adjacent caudal vertebrae (Cd7-Cd10); 2) a sham group (n=5) in which the rats had an incision at the site where the device would have been implanted on Cd7 to Cd 10; and 3) a control group (n=5) in which the rats had no surgery at all (n refers to the number of rats in the groups).

The rats were operated at the age of 26 days and kept alive for 7 weeks. They were anaesthetized by isoflurane (induction at 3-4%, maintained at 2-3% during the procedure) and the surgeries were done under a binocular microscope.

For the rats of the experimental group (group 1), an incision was done between the intervertebral disc and the bony endplate. The prong 12 of the device 10 was inserted into this incision and the device 10 fixed to the vertebra with a screw 20, of a length of 3 or 4 mm depending on the size (width) of the operated vertebra. The skin was then continuously sutured.

The rats of group 2 (sham) had the same intervention, but without the implantation of the device and screw.

In these first two groups, post-operative pain control was performed by buprenorphine injections (subcutaneous, 0.1-0.5 mg/kg). Operated rats were radiographed before and after the surgery as well as at every 12 days afterwards, and each time, in the same ventral decubitus position for a posteroanterior radiograph.

All radiographs were digitized and analyzed using dedicated image analysis software (SliceOMatic™, version 4.2; Tomovision, Montreal, QC, Canada). Global deformations were measured with the Cobb method on the Cd7-Cd10 segment (angle from the superior endplate of the proximal instrumented vertebra to the inferior endplate of the distal instrumented vertebra). Local measurement on Cd6 to Cd11 was also done: vertebral wedging was measured by fitting a line on the proximal vertebral plate and one on the distal vertebral plate. The angle between these two lines was the wedging angle. The vertebral heights were also measured in the middle of the vertebrae.

After sacrifice ($CO_2$), all rat tails were radiographed using a high resolution radiographic system (Faxitron™ MX-20, Faxitron X-ray Corporation, Wheeling Ill., USA). CT Scans were performed on three samples using a desktop micro-CT instrument (Model 1072, Skyscan™, Aartselaar, Belgium). Samples were scanned at a magnification resulting in a pixel size of 15.95 µm. The cross-sections along the specimen axis were reconstructed using NRecon Software (SkyScan™), with a distance between each cross-section of 31.90 µm.

For histological purposes, the tissues were fixed in formaldehyde and dehydrated in solutions with increasing alcohol concentrations. Tissues were cleared in xylene and then embedded in methyl methacrylate solutions (MMA) with increasing concentrations of polymerization agent.

Eight specimens showing at least 3 harvested vertebrae (6 specimens of the experimental group presenting significant deformation, 1 of the sham group and 1 of the control group) were prepared for histological observation and measurement of the bone, cartilage, disc and fibrous tissue around the device. The cutting/grinding method was used to cut thick slices (30-40 µm) containing the implanted device using the Technovit™ 7200 (EXAKT Technologies, Inc. Oklahoma City, Okla.) and the slices were coloured with Toluidine blue.

Eight blocs of tissues were selected to be analysed for descriptive histological analysis. Six of them came from instrumented animals (resulting in 16 intervertebral discs), one from a sham animal (with 3 intervertebral discs) and one from a control (with 3 intervertebral discs). The blocs coming from instrumented animals had two or three histological slices prepared and the ones from the sham and control groups had each one slice. Pictures of the intervertebral discs were taken using an optical microscope (Leika™ DMR) and classified into three categories: discs with no visible alteration, discs showing fibrous tissues and discs showing alterations like a hernia.

In order to quantify the growth-suppressing influence of the implanted device, tetracycline and calcein stains were injected at 12 day interval during the post-op follow-up. Distances between stains were then measured under appropriate magnification and compared between experimental groups (SliceOMatic™, version 4.2; Tomovision, Montreal, QC, Canada).

Finally, to analyse the influence of the implanted device on the bone itself, a histomorphometric analysis was performed on slices of 6 µm taken from 18 vertebral sections (10i, 4s, 4c). The presence of fibrous tissue, the trabecular number and thickness were quantified over several cross sections of each vertebra (using software Bioquant Nova Prime 6.9, for example).

Nine of the animals from the experimental group and all of the others were followed during an entire 7 week period. One pre-operative ("pre-op") death occurred because of anaesthesia. One of the instrumented rats had to be sacrificed because of severe post-operative ("post-op") infection. Five animals had minor post-op infections which were healed within 2 days by local antibiotics (Polysporin Ophthalmic ointment was used for example).

Figure 2:
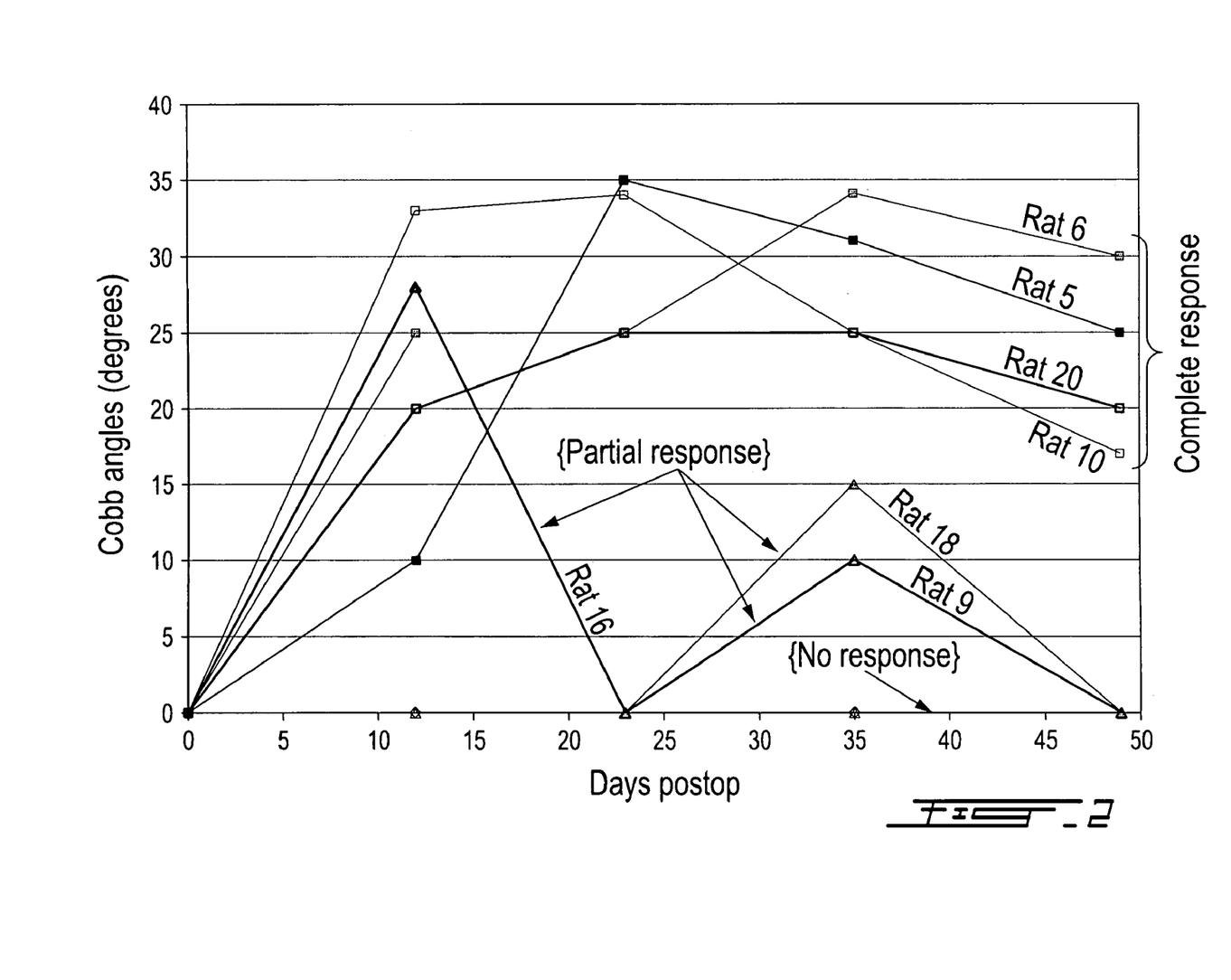
FIG. 2 shows Cobb angles versus time post-op for all the rats of the experimental group.

The nine animals from the experimental group were divided into 3 subgroups depending on their growth modulation response. FIG. 2 shows the "complete response" subgroup (n=4), in which the device 10 induced a growth modulation response from the first radiograph taken after the day of surgery until the sacrifice; the "partial response" subgroup (n=3), in which the device 10 induced a growth modulation response over a short period of time, which was observed on only one radiograph; and the "non response" subgroup (n=2), in which the device 10 induced no growth modulation response at all.

Figure 3:
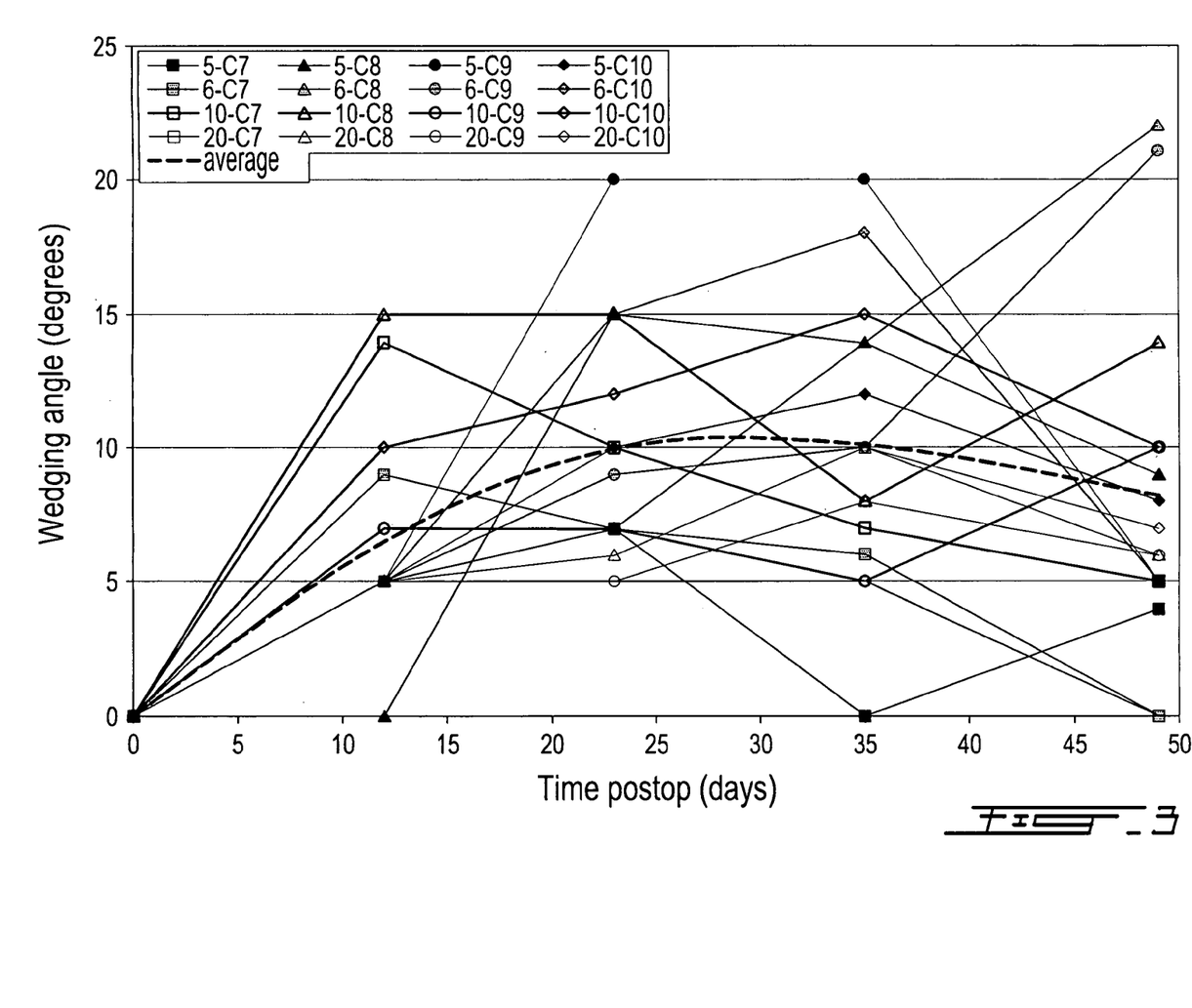
FIG. 3 shows vertebral wedging of versus time; $7^{th}$ to $10^{th}$ vertebrae are plotted for the four rats from complete response subgroup.

The complete response subgroup showed vertebral wedging angles in the instrumented vertebrae which reached maxima of 22°, 20°, 15° and 10° between 12 and 35 days post-op (FIGS. 1 and 3). These local growth modulations lead to global deformations, as may be seen in FIG. 4. The maximum Cobb angle of 35° was obtained 23 days post-op in one of the four rats, the other had maximums of 34°, 34° and 25° between 23 and 35 days post-op (FIG. 2). The spinal curve was slightly reduced to an average of 23° after 49 days post-op.

In the partial response subgroup, a spinal curvature was induced after the instrumentation: 28° (12 days post-op), 10° and 15° (35 days post-op) but disappeared subsequently (FIG. 2).

In the sham group, three had no deformity at all while two had a small deformity (10° and 16°) 12 days post-op. These angles were significant compared to the absence of angle in the control group (p=0.01) but they disappeared within the next 12 days.

FIG. 1 shows a 3D reconstruction after microCT Scan. The device 10 is in a position efficient for growth modulation. The vertebral wedging of this vertebra is about 14°.

Figure 5:
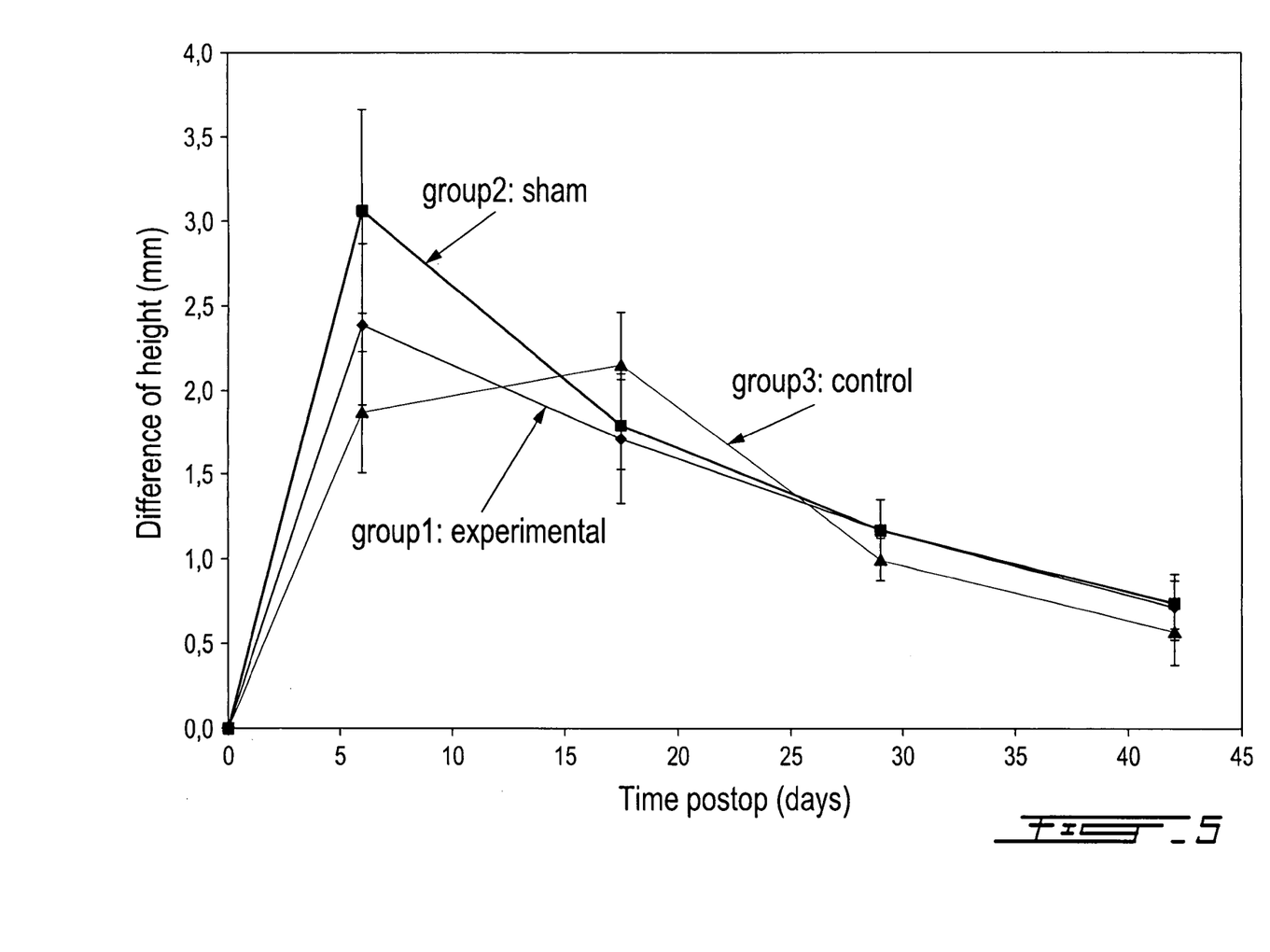
FIG. 5 illustrates the growth rate versus days post-op for the rats of all three experimental groups.

As shown in FIG. 5, the sham and experimental groups had their growth peak at the same time within the first 12 days post-op, the former being significantly larger than the latter (3.1 mm±0.6 versus 2.4 mm±0.5). The control group had its growth peak later (12-23 days post-op) with an average of 2.2 mm±0.3.

Figure 7A:
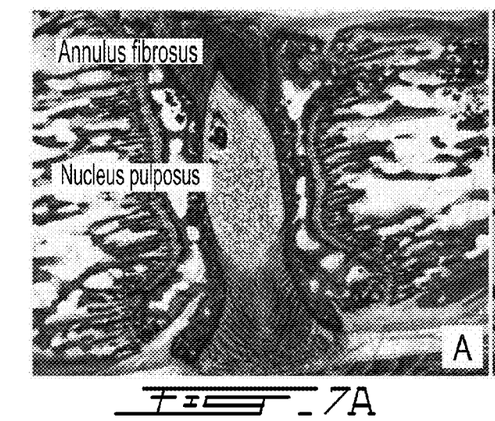
FIG. 7 show a) intervertebral disc showing no visible alteration; b) deformed intervertebral disc showing no visible alteration; c) intervertebral disc with fibrous tissues; d) intervertebral disc with an hernia.
Figure 7B:
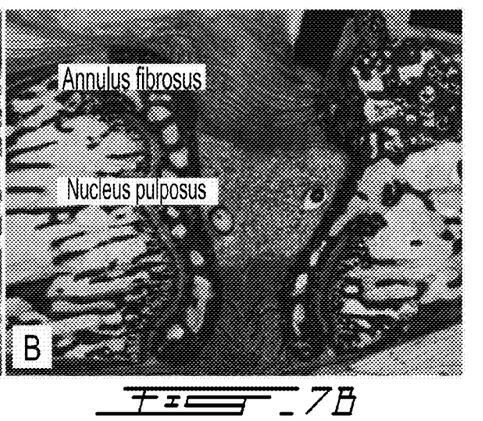
Figure 7C:
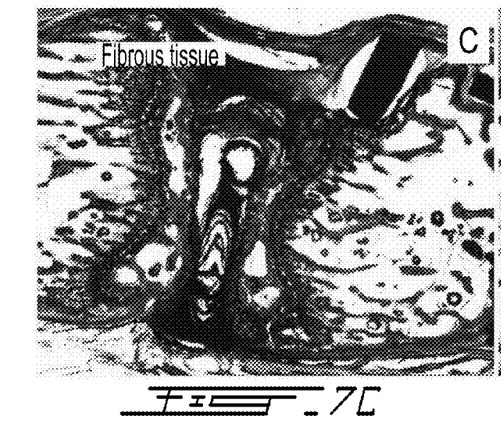
Figure 7D:
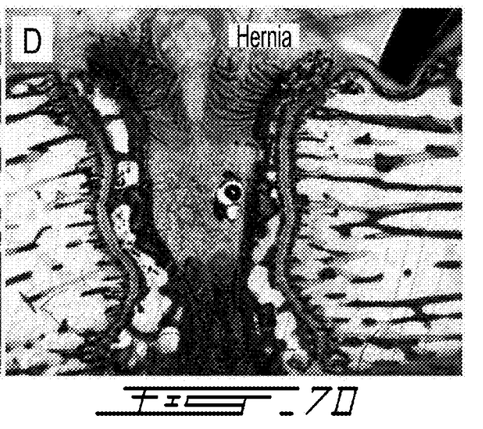

The 22 images of the 8 selected intervertebral discs were analyzed using descriptive histology and were classified into three categories. As shown in FIG. 7a, eleven of the 16 images from the instrumented vertebrae showed no visible alteration, with four of them being deformed but not altered (FIG. 7b). As for the remaining five images from the instrumented group, three of them showed fibrous tissues (FIG. 7c) and two showed a hernia (FIG. 7d). The three discs from the sham group and the three discs from the control groups showed no alteration at all.

Calcification staining was evident within the growth plate between the $35^{th}$ and $49^{th}$ day. Each cross section observed demonstrated a growth reduction with a mean value of 14% (500 μm). Histomorphometric analysis returned consistent readings for both the trabecular number and thickness. Mean values of 2.8±0.3 per/mm and 50 mcm (micrometers, standard unit for trabecular thickness)±10 were measured for the trabecular number and thickness respectively.

The present study demonstrated the feasibility of a fusionless growth modulation technique on a rat tail model. Significant spinal deformities were induced to the caudal vertebrae by the device 10. Global deformations reached a maximum of 35° and vertebral deformities a maximum of 22°.

Decreasing deformities were observed at the end of the experience. It is thought that the strength and growth of the vertebral growth plate, in conjunction with appositional growth, pushed the device 10 out of its position, until the vertebra overgrows the device 10.

The observed outward displacement of the device 10 often occurred along a direction angulated compared to an initial direction of the device. It is though that, as the vertebra grows, it exerts forces on the prong 12, and the connection of the device to the vertebra by the screw 14 acting as a pivot, the prong 12 tilts while the remaining of the device is maintained in its original direction relative to the vertebral body by the screw 20.

Because of such a pivot action, the effect of the device 10 has a limited time effect, which could be used for targeted scoliosis treatments. Indeed, in some cases, there is need to modulate the growth of the growth of a vertebral body only during a limited period of time, which could correspond to the time the device takes to tilt position, for example. On the contrary, in cases where a continued action of the device is required, additional screws could be provided to prevent the titling effect.

Figure 6A:
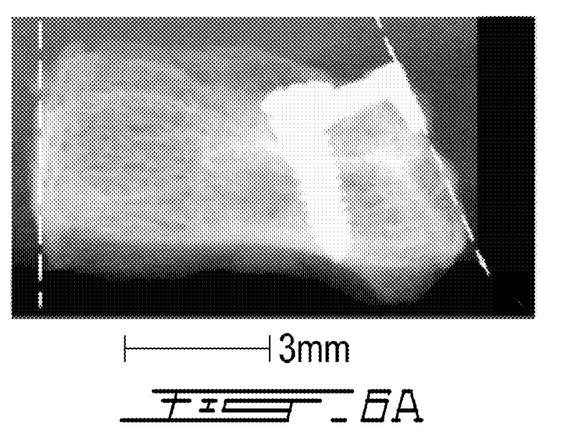
FIG. 6 are high resolution radiographs showing the position of 3 devices: A) efficient position, B) position of the device being pushed out by the vertebra, C) inefficient position.
Figure 6B:
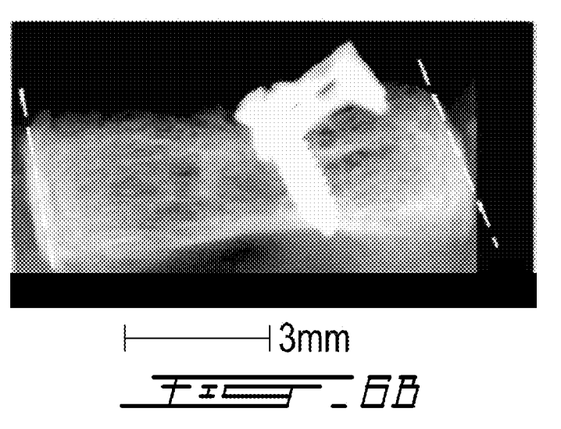
Figure 6C:
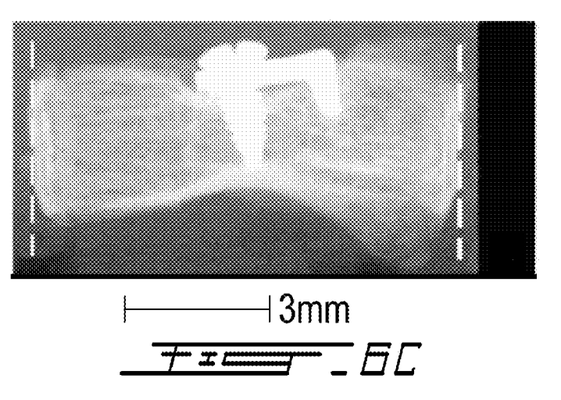

An efficient growth modulation requires a proper positioning of the device 10. FIG. 6 show 3 typical device positions, including A) a proper and efficient position, B) a position resulting in the device 10 being overgrown by the vertebra, and C) a device 10 in an inadequate and inefficient position. Improperly positioned devices did not produce a growth modulation.

Animals from the sham group showed no significant long term growth modulation. A local disturbance, with no device implanted to compress the growth plate of the vertebral body, did not induce a significant long term growth modulation. However, this local disturbance may cause increased blood flow and cellular activity around the wound, which could have lead to the highest growth peak of all the three test groups. The same increased blood flow was present in the experimental group but the device slowed the growth down. The growth peak of the control group appeared later around the age of 40 days as reported by others[10,11].

The alteration of the discs was probably due to the surgical procedure. The incision that should have helped the insertion of the device might have been done in the intervertebral disc, which leads to a clear hernia. One of the herniated discs came from an animal from the complete response subgroup regarding the growth modulation response (see vertebra 20C7, FIG. 3). Although the global deformity of this tail was important, the local wedging of the herniated vertebra reached a maximum of 5 degrees and ended with no wedging. The other herniated disc came from an animal from the partial response subgroup (Rat 16).

The three discs that showed fibrous tissues all came from Rat 5, which is the one having the maximal growth modulation of all. The fast growing of the curvature, which reached a maximum of 35 degrees, may have induced this fibrous tissue and a loss of mechanical function. None of the other discs showed alteration.

Moreover, it is to be noted that, although the animals were always positioned in the same way during the X-Rays (ventral decubitus), the position of their tails may have varied slightly from one radiograph to the other. Furthermore the orientation of the devices was not exactly the same in all the animals. The errors of measurement were estimated to 5 degrees for the wedging because smaller angles were not measurable. Even so, the local and global deformations induced by this device were significant and appeared in short times.

Measurements taken from the staining process showed consistent suppression of growth rate under action of the implant, when compared to other areas. This demonstrated the success of the implanted device as a means to locally manipulate longitudinal bone growth. Moreover, results from the histomorphometric study showed absence of fibrous tissue around the screw of the implanted device. Results also showed no significant statistical difference between trabecular number and thickness between all experimental groups. These results provide evidence of successful osseo-integration of the device and high structural integrity.

Therefore, it is shown that a device according to the present invention, when properly positioned, induces a significant controlled wedging of the vertebrae, while maintaining spinal flexibility, the intervertebral disc being un-altered.

Such a device and associated method may be tested on larger animal models and then possibly transferred and adapted to humans with the clinical strategic goal of early treatment of scoliosis by controlled modulation of vertebral growth.

Figure 8A:
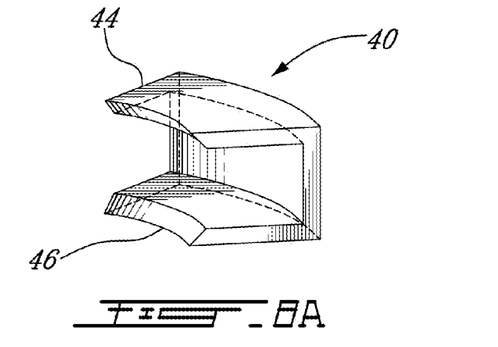
FIGS. 8-10 show devices according to further embodiments of the present invention.
Figure 8B:
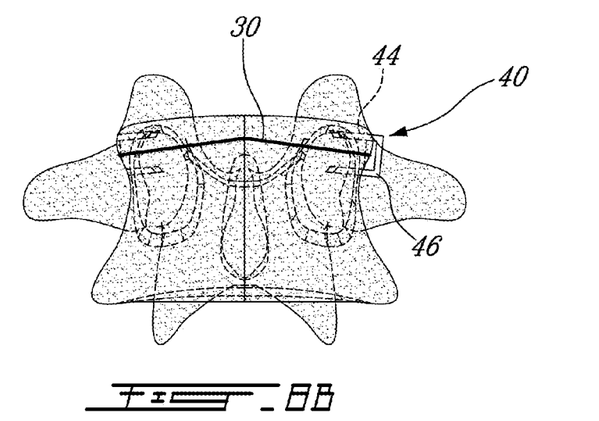

FIG. 8a shows an alternative embodiment of a device of the present invention. The device 40 comprises a first prong 44 located between the growth plate of the vertebral body and the intervertebral disk, and a second prong 46 anchored in the vertebral body, thereby spanning a side of the growth plate 30 of the vertebral body therebetween, as a staple, and applying a compression on this side (right hand side in FIG. 8b) of the growth plate 30 of the vertebral body as it grows, and slowing down the growth thereof on this compressed side.

Figure 8C:
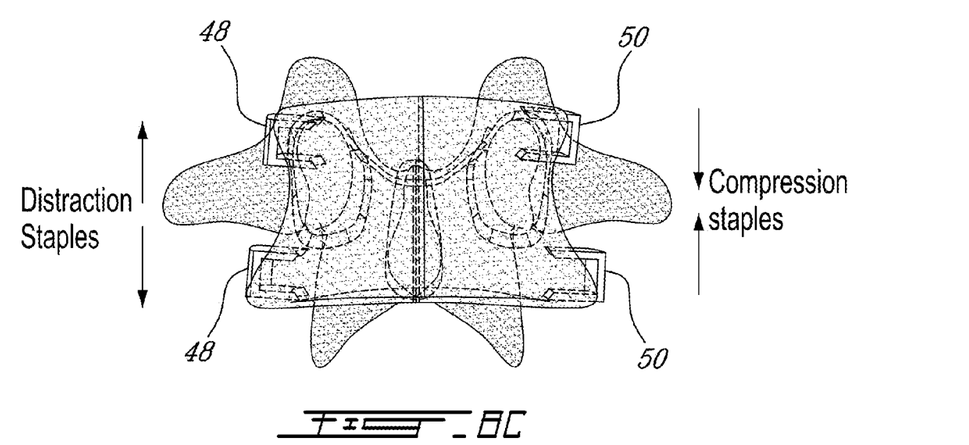

Alternatively, the device may be used to apply tension on a side on a given growth plate of a vertebral body for purpose of accelerating the growth on the instrumented side of this growth plate. In FIG. 8c for example, the devices 50 apply a compression on the right hand side of the growth plates of the vertebral body, while the devices 48 positioned on the opposite side of the same growth plates, apply a tension of this side of the growth plates: as a result growth of the growth of the vertebral body is hindered on the right hand side, whereas it is favoured on the left hand side.

Figure 9:
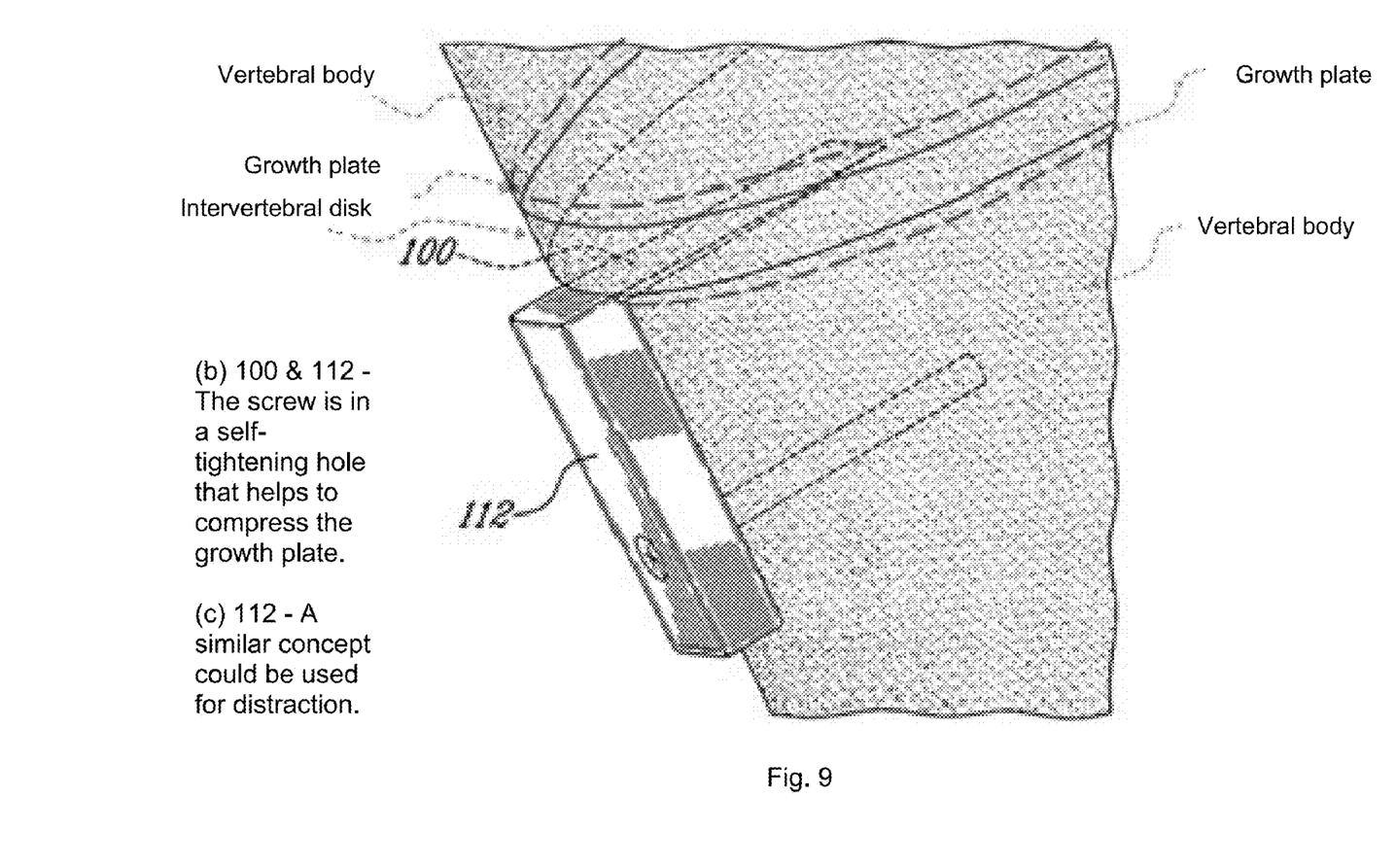
Figure 10A:
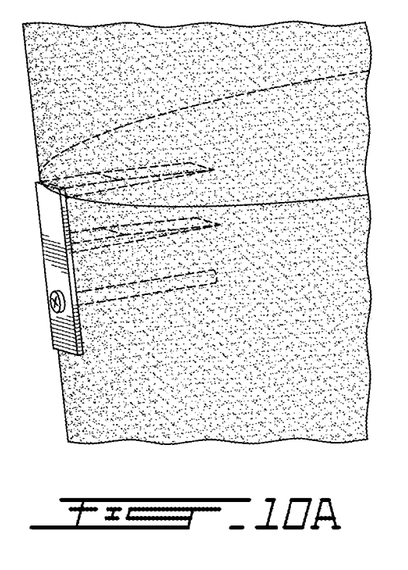
Figure 10B:
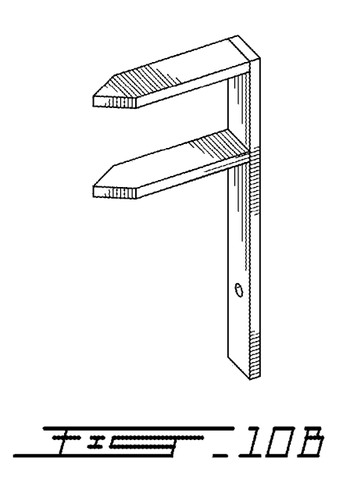
Figure 10C:
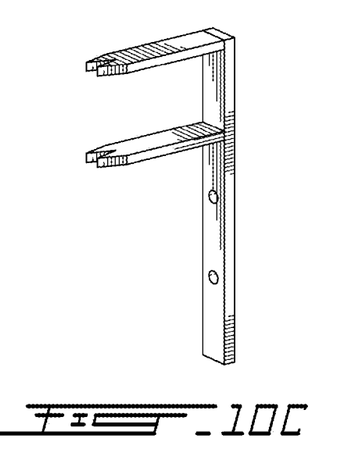
Figure 10D:
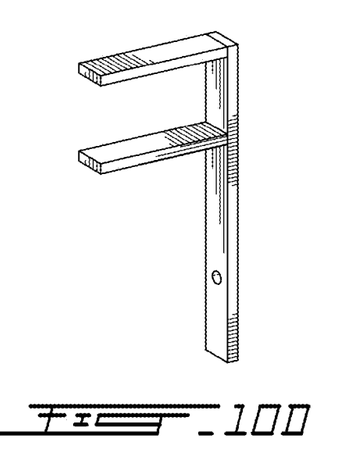
Figure 10E:
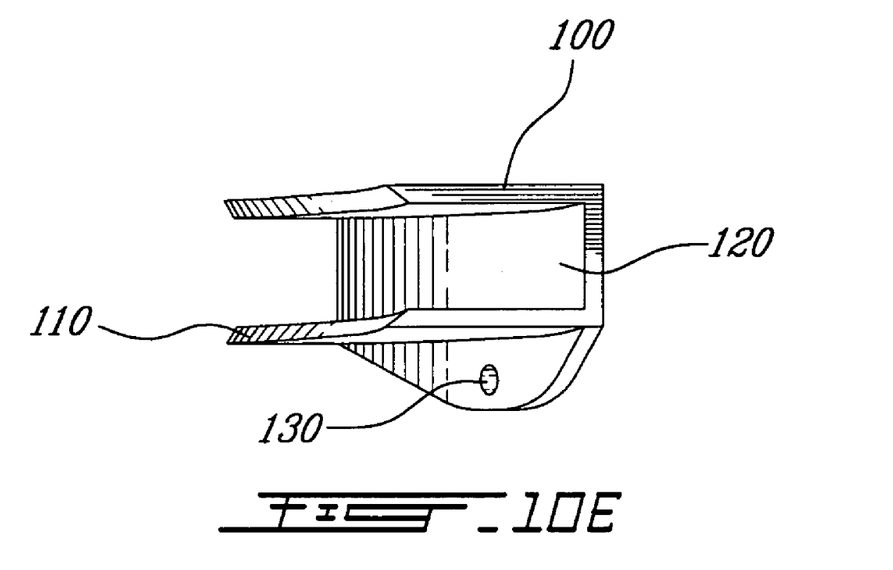
Figure 10F:
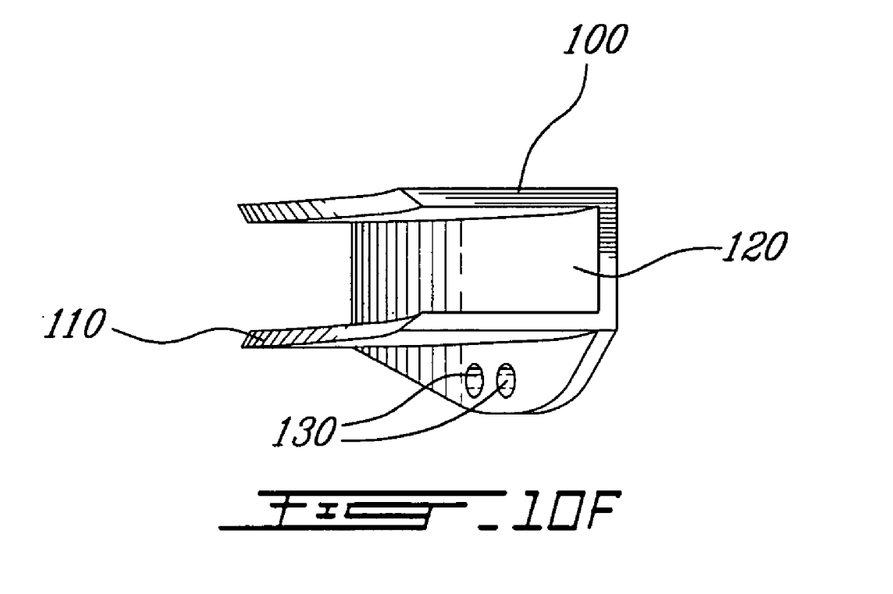

FIGS. 9 and 10 illustrate other embodiments of a device according to the present invention.

The part 100 of the device in contact with the growth of a vertebral body is typically plate-shaped, so as to exert a force on the growth plate of a vertebral body. The part 110 of the device anchored in the bone projects inside the bone and is retained there.

In FIG. 9, a screw in a self-tightening hole is used as the part 110, and depending on its orientation, the screw may be used to compress the growth plate of the vertebral body (FIG. 9b) or to exert tension thereon (FIG. 9c).

In FIG. 10, the part 100 is shown as a first prong and the part 110 is shown as a second prong, the two parts being connected by a side wall 120, the side wall receiving lateral fixations 130 to the bone.

The device of the present invention may be made in a range of biocompatible materials, including titanium (grade 5, 6Al4V) or surgical stainless steel for example, shape memory alloy, etc . . . .

The device of the present invention may be made in a static, i.e. non-deformable, material, so that once positioned, the length of material between the first and second parts thereof does not vary whereas the growth plate of the vertebral body tends to grow, thereby exerting a compressive stress on the growth plate of the vertebral body.

The device of the present invention may also be made in a shape memory alloy, so that the length of material between the first and second parts thereof recovers a pre-determined length once the device is positioned, due to temperature changes. In the case of a length when inserted less that this pre-determined length, the device once positioned thus exerts a tension on the growth plate of the vertebral body, whereas in the case when the length when inserted is larger that this pre-determined length, the device once positioned tends to exert compression on the growth plate of the vertebral body and acts as a growth stopper on one side during the vertebral growth.

Other biocompatible material may be used, allowing for example positioning of the device in a pre-stressed condition, so that the device exerts tension on the growth plate of the vertebral body once positioned, or in a pre-tensed condition, so that it exerts a compressive stress on the growth plate of the vertebral body once positioned, depending on the growth modulation desired.

In term of surgical procedure, the device is adapted to be implanted on the periphery of the vertebra, in a minimally invasive way, as known in the art.

The compressive stress or tension induced on the growth of the vertebral body by the device modulates its growth. Therefore, when implanted on a wedged vertebra, such as for instance in scoliotic spines, the device reduces the wedging of wedged vertebra and therefore reduces the global deformity of the spine. As mentioned hereinabove, the duration of such action of the device in time may be varied.

There is provided a minimally invasive and fusionless device and method allowing acting on vertebral growth of a vertebral body without crossing the intervertebral disc. As a result, as in the case of bracing for example, the present device and method allow preserving growth, motion, and function of the spine, while, as is the case when using surgery for example, they provide a substantial correction of deformity. Moreover, they may avoid adjacent segment degeneration and other complications related to fusion for example.

Although the present invention has been described hereinabove by way of specific embodiments thereof, it can be modified, without departing from the spirit and nature of the subject invention as defined in the appended claims.

REFERENCES

1. Betz R R, Kim J, D'Andrea L P et al. An Innovative Technique of Vertebral Body Stapling for the Treatment of Patients with Adolescent Idiopathic Scoliosis: A Feasibility, Safety and Utility Study. *Spine* 2003; 28:S255-S265
2. Betz R R, D'Andrea L P, Mulcahey M J et al. Vertebral Body Stapling Procedure for the Treatment of Scoliosis in the Growing Child. *Clinical Orthopaedics and Related Research* 2005; 434:55-60.
3. Wall E J, Bylski-Austrow D I, Kolata R J et al. Endoscopic Mechanical Spinal Hemiepiphysiodesis Modifies Spine Growth *Spine,* 2005; 30:10, 1148-1153
4. Braun J T, Akyuz E, Udall H et al. Three-Dimensional Analysis of 2 Fusionless Scoliosis Treatments: A Flexible Ligament Tether versus a Rigid-Shape Memory Alloy Staple *Spine* 2006; 31:3, 262-268
5. Braun J T, Ogilvie J W, Akyuz E et al Creation of an Experimental Idiopathic-Type Scoliosis in an Immature Goat Model Using a Flexible Posterior Asymmetric Tether *Spine* 2006; 31: 13, 1410-1214
6. Akyuz E, Braun J T, Brown N A T et al Static Versus Dynamic Loading in the Mechanical Modulation of Vertebral Growth *Spine,* 2006; 31:25, E952-E958
7. Grunhagen T, Wilde G, Soukane D M et al. Nutrient Supply and Intervertebral Disc Metabolism *J. Bone Joint Surg. Am.* 2006; 88:30-35
8. Stokes I A F, Gwadera J, Dimock A et al. Modulation of vertebral and tibial growth by compression loading: diurnal versus full-time loading. *Journal of Orthopaedic Research* 2005; 23:188-195.
9. Stokes I A F, Spence H, Aronsson D D et al. Mechanical Modulation of Vertebral Body Growth: Implications for Scoliosis Progression. *Spine* 1996; 21:1161-1167.
10. Hunziker E B, Schenk R K, Physiological Mechanisms adopted by chondrocyte regulating longitudinal bone growth in rats *Journal of Physiology* 1989; 414: 55-71
11. Alvarez J, Balbin M, Santos F et al. Different bone growth rates are associated with changes in the Expression Pattern of Types II and X collagens and Collagenace 3 in Proximal Growth Plates of the Rat Tibia *Journal of Bone and Mineral Research* 2000; 15:1, 82-94.

The invention claimed is:

1. A method for modulating growth of a target growing vertebral body of a spine, by:

inserting a first part between a growth plate of the target vertebral body and an associated intervertebral disc on a first side of the spine and in contact with both said growth plate and said adjacent intervertebral disk; and securing the first part in contact with the growth plate of the vertebral body and the adjacent intervertebral disk by anchoring a second part to the vertebral body, the second part being connected to the first part by a length of material thereby capturing the growth plate between the first part and the vertebral body;

the first part being adapted to apply a force on the growth plate of the vertebral body on the first side of the spine as the vertebral body grows, retarding the longitudinal growth of the growth plate on the first side of the vertebra while permitting unrestrained growth of the growth plate on a second side of the spine opposite the first side of the spine.

2. The method of claim 1, wherein said inserting a first part comprises inserting a prong and said anchoring a second part comprises securing a screw through said length of material into the vertebral body, whereby the prong applies a force on the growth plate of the vertebral body as said vertebral body grows.

3. The method of claim 1, wherein the length of material is made in one of:

i) a static material, ii) a pre-stressed material and iii) a pre-tensed material.

4. The method of claim 1, wherein the length of material is made in a shape-memory alloy.

5. The method of claim 1, comprising inserting the first part along at least part of the width of the growth plate of the vertebral body on a convex side of the spine.

6. The method of claim 1, comprising inserting the first part along at least part of the width of the growth plate of the vertebral body on a concave side of the spine.

\* \* \* \* \*